(12) United States Patent
Reddington et al.

(10) Patent No.: US 8,956,523 B2
(45) Date of Patent: Feb. 17, 2015

(54) METAL PLATING COMPOSITIONS AND METHODS

(71) Applicants: Erik Reddington, Ashland, MA (US);
Gonzalo U. Desmaison, Berlin (DE);
Zukra I. Niazimbetova, Westborough, MA (US); Donald E. Cleary, Littleton, MA (US); Mark Lefebvre, Hudson, NH (US)

(72) Inventors: Erik Reddington, Ashland, MA (US);
Gonzalo U. Desmaison, Berlin (DE);
Zukra I. Niazimbetova, Westborough, MA (US); Donald E. Cleary, Littleton, MA (US); Mark Lefebvre, Hudson, NH (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 133 days.

(21) Appl. No.: 13/621,285

(22) Filed: Sep. 16, 2012

(65) Prior Publication Data

US 2014/0081045 A1    Mar. 20, 2014

Related U.S. Application Data

(62) Division of application No. 13/226,290, filed on Sep. 6, 2011, now Pat. No. 8,329,018.

(51) Int. Cl.
*C25D 3/56* (2006.01)
*C25D 3/62* (2006.01)
*C25D 3/00* (2006.01)
*C25D 3/46* (2006.01)

(52) U.S. Cl.
USPC ............ 205/238; 205/239; 205/241; 205/242

(58) Field of Classification Search
USPC .................................. 205/238, 239, 241, 242
See application file for complete search history.

(56) References Cited

U.S. PATENT DOCUMENTS

| | | | |
|---|---|---|---|
| 3,518,067 A | 6/1970 | Barth et al. | |
| 4,406,875 A | 9/1983 | De Jong et al. | |
| 3,230,183 A | 1/1996 | Valko et al. | |
| 6,294,697 B1 | 9/2001 | Wilbur et al. | |
| 6,425,996 B1 | 7/2002 | Dahms et al. | |
| 8,012,334 B2 * | 9/2011 | Reddington et al. | 205/239 |
| 2003/0066756 A1 | 4/2003 | Gabe et al. | |
| 2007/0120910 A1 | 5/2007 | Odell et al. | |
| 2007/0123606 A1 | 5/2007 | Toma et al. | |

FOREIGN PATENT DOCUMENTS

| | | | |
|---|---|---|---|
| EP | 0 794 211 A2 | 10/1997 | |
| EP | 0 794 211 A3 * | 4/1998 | ............ C08G 69/44 |
| GB | 797175 | 6/1958 | |
| JP | 57-109993 | 1/1984 | |

* cited by examiner

*Primary Examiner* — Kamal Saeed
*Assistant Examiner* — Janet L Coppins
(74) *Attorney, Agent, or Firm* — John J. Piskorski

(57) ABSTRACT

Disclosed are metal plating compositions and methods. The metal plating compositions provide good leveling performance and throwing power.

1 Claim, No Drawings

METAL PLATING COMPOSITIONS AND METHODS

This application is a Divisional of U.S. Non-Provisional application Ser. No. 13/226,290, filed Sep. 6, 2011, which application claims the benefit of U.S. Non-Provisional application Ser. No. 12/080,522, filed Apr. 2, 2008, now U.S. Pat. No. 8,012,334, which application claims the benefit of priority under 35 U.S.C. §119(e) to U.S. Provisional Application No. 60/921,599, filed Apr. 3, 2007, the entire contents of which application are incorporated herein by reference.

The present invention is directed to metal plating compositions and methods. More specifically, the present invention is directed to metal plating compositions and methods which provide improved leveling and throwing power.

Metal plating is a complex process that involves multiple ingredients in a plating composition. In addition to metal salts and other ions, which provide a source of metal and ionic conductivity, other components include additives to improve the brightness, ductility and plating distribution of the metal deposit. Such additives may include surfactants, brighteners, carriers and levelers.

Uniform distribution of a metal on a substrate is necessary, such as in the metallization of printed wiring boards which has a surface layer as well as a number of through-holes and blind vias. If only a thin layer of metal is deposited in these through-holes and blind vias, it may tear under thermal or mechanical stress, for example during soldering, such that the passage of current is interrupted. This type of failure would produce a printed wiring board that is unacceptable for use in an electronic application. Since printed wiring boards with smaller and smaller hole diameters are being manufactured, for example 0.25 mm and smaller, it becomes more and more difficult to simultaneously electroplate an evenly distributed layer of metal onto the surface and into the through-holes. It has been observed that metal layer thickness is unsatisfactory in many printed wiring boards, particularly in holes with small diameters. Achieving a bright metal layer of uniform thickness with high thermal reliability can be challenging for many circuit board designs.

Many plating formulations use a chemical solution to address the problem of non-uniform plating by adding levelers to the plating bath. Various compounds have been used with varying performance. An example of one type of leveler used in copper plating baths are the transformation products formed from epihalohydrins, dihalohydrins or 1-halogen-2,3-propandiols and polyamidoamines as disclosed in U.S. Pat. No. 6,425,996. Another example of levelers are those disclosed in Japanese patent S63-52120. These levelers are ethoxylated dicarboxylic acids and ethoxylated diamines. While the compounds disclosed in these two patents allegedly have acceptable leveling performance, there is still a need for compounds which improve metal plating performance.

In one aspect the invention includes compounds having a general formula:

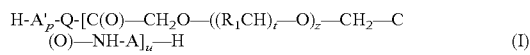
(I)

where A' is —(NH—($CH_2$)$_{x'}$)$_{y'}$—; —NH($CH_2$)$_{x'}$—(O—($CHR_1$)$_{r'}$)$_{w'}$—O—($CH_2$)$_{x'}$—; or —NH—(($R_1$CH)$_{r'}$—O)$_{w'}$—$C_2H_4$—;
A is —(($CH_2$)$_x$—NH)$_y$—; —($CH_2$)$_x$—(O—($CHR_1$)$_r$)$_w$—O—($CH_2$)$_x$—NH—; or —(($R_1$CH)$_r$—O)$_w$—$C_2H_4$—NH—;
$R_1$ is —H or —$CH_3$,
Q is —NH— when p=1 or —O— when p=0,
p is 0 or 1, wherein H— and Q form a chemical bond when p=0,
r' is an integer from 2 to 4,
w' is an integer from 1 to 50,
x' is an integer from 2 to 6,
y' is an integer from 0 to 5,
wherein H— and Q form a chemical bond when y' is 0,
r is an integer from 2 to 4,
w is an integer from 1 to 50,
x is an integer from 2 to 6,
y is an integer from 0 to 5, wherein H— is bonded to the nitrogen of terminal —C(O)—NH— when y is 0,
t is an integer from 2 to 4,
u is an integer from 1 to 20,
w is an integer from 1 to 50, and
z is an integer from 1 to 50.

In another aspect the invention includes a metal plating composition including one or more sources of metal ions and one more compounds having a formula:

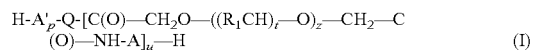
(I)

where A' is —(NH—($CH_2$)$_{x'}$)$_{y'}$—; —NH($CH_2$)$_{x'}$—(O—($CHR_1$)$_{r'}$)$_{w'}$—O—($CH_2$)$_{x'}$—; or —NH—(($R_1$CH)$_{r'}$—O)$_{w'}$—$C_2H_4$—,
A is —(($CH_2$)$_x$—NH)$_y$—; —($CH_2$)$_x$—(O—($CHR_1$)$_r$)$_w$—O—($CH_2$)$_x$—NH—; or —(($R_1$CH)$_r$—O)$_w$—$C_2H_4$—NH—,
$R_1$ is —H or —$CH_3$,
Q is —NH— when p=1 or —O— when p=0,
p is 0 or 1, wherein H— and Q form a chemical bond when p=0,
r' is an integer from 2 to 4,
w' is an integer from 1 to 50,
x' is an integer from 2 to 6,
y' is an integer from 0 to 5,
wherein H— and Q form a chemical bond when y' is 0,
r is an integer from 2 to 4,
w is an integer from 1 to 50,
x is an integer from 2 to 6,
y is an integer from 0 to 5, wherein H— is bonded to the nitrogen of terminal —C(O)—NH— when y is 0,
t is an integer from 2 to 4,
u is an integer from 1 to 20,
w is an integer from 1 to 50, and
z is an integer from 1 to 50.

In a further aspect the invention includes a method including: providing metal plating compositions including one or more sources of metal ions and one or more compounds having a formula:

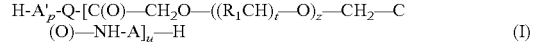
(I)

where A' is —(NH—($CH_2$)$_{x'}$)$_{y'}$—; —NH($CH_2$)$_{x'}$—(O—($CHR_1$)$_{r'}$)$_{w'}$—O—($CH_2$)$_{x'}$—; or —NH—(($R_1$CH)$_{r'}$—O)$_{w'}$—$C_2H_4$—,
A is —(($CH_2$)$_x$—NH)$_y$—; —($CH_2$)$_x$—(O—($CHR_1$)$_r$)$_w$—O—($CH_2$)$_x$—NH—; or —(($R_1$CH)$_r$—O)$_w$—$C_2H_4$—NH—;
$R_1$ is —H or —$CH_3$,
Q is —NH— when p=1 or —O— when p=0,
p is 0 or 1, wherein H— and Q form a chemical bond when p=0,
r' is an integer from 2 to 4,
w' is an integer from 1 to 50,
x' is an integer from 2 to 6,
y' is an integer from 0 to 5,
wherein H— and Q form a chemical bond when y' is 0,
r is an integer from 2 to 4, w is an integer from 1 to 50, x is an integer from 2 to 6, y is an integer from 0 to 5, wherein H— is bonded to the nitrogen of terminal —C(O)—NH— when y is 0, t is an integer from 2 to 4, u is an integer from 1 to 20, w is an integer from 1 to 50, and z is an integer from 1 to 50; contacting a substrate with the compositions; and depositing a metal on the substrate.

The water-soluble compounds may be used in metal plating compositions in any industry where metal plating is done. For example, the metal plating compositions may be used in the manufacture of electrical devices, such as printed wiring boards, in general, through-holes, vias, integrated circuits, electrical contact surfaces and connectors, electrolytic foil, silicon wafers for microchip applications, semi-conductors and semi-conductor packaging, solar cell, lead frames, opto-electronic devices and packaging and solder bumps. The metal plating compositions also may be used for metal plating decorative articles, such as jewelry, furniture fittings, automobile parts and sanitary appliances.

As used throughout this specification, the following abbreviations shall have the following meanings, unless the context indicates otherwise: ° C.=degrees Centigrade; g=gram; mg=milligrams; L=liter; ml=milliliter; dm=decimeter; A=amperes; mm=millimeters; cm=centimeters; ppb=parts per billion; ppm=parts per million; mbar=millibar; mil=0.001 inches; 2.54 cm=1 inch; wt %=percent by weight; NMR=nuclear magnetic resonance; SEC=size exclusion chromotography; and "throwing power"=The ratio of the thickness of the metal plated in the center of a through hole compared to the thickness of the metal plated at the surface. All percentages are by weight, unless otherwise noted. All molecular weights are in grams/mole unless otherwise noted. All numerical ranges are inclusive and combinable in any order, except where it is logical that such numerical ranges are constrained to add up to 100%.

The compounds have a general formula:

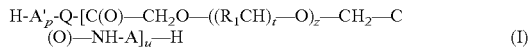
(I)

where A' is —(NH—$(CH_2)_{x'}$)$_{y'}$—; —NH$(CH_2)_{x'}$—(O—$(CHR_1)_{r'}$)$_{w'}$—O—$(CH_2)_{x'}$—; or —NH—($(R_1CH)_{r'}$—O)$_{w'}$—$C_2H_4$—, A is —(($(CH_2)_x$—NH)$_y$; —$(CH_2)_x$—(O—$(CHR_1)_r$)$_w$—O—$(CH_2)_x$—NH—; or —(($R_1CH)_r$—O)$_w$—$C_2H_4$—NH—, $R_1$ is —H or —$CH_3$, Q is —NH— when p=1 or —O— when p=0, p is 0 or 1, wherein H— and Q form a chemical bond when p=0, r' is an integer from 2 to 4 or such as from 2 to 3, w' is an integer from 1 to 50 or such as from 1 to 40 or such as from 2 to 35, x' is an integer from 2 to 6 or such as from 2 to 3, y' is an integer from 0 to 5 or such as from 2 to 3, wherein H— and Q form a chemical bond when y' is 0, r is an integer from 2 to 4 or such as from 2 to 3, w is an integer from 1 to 50 or such as from 1 to 40 or such as from 2 to 35, x is an integer from 2 to 6 or such as from 2 to 3, y is an integer from 0 to 5 or such as from 2 to 3, wherein H— is bonded to the nitrogen of terminal —C(O)—NH— when y is 0, t is an integer from 2 to 4 or such as from 2 to 3, u is an integer from 1 to 20 or such as from 1 to 10, w is an integer from 1 to 50 or such as from 1 to 40 or such as from 2 to 35, and z is an integer from 1 to 50 or such as from 1 to 40 or such as from 1 to 16.

Typically the compounds include those having a general formula:

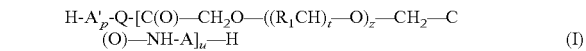
(I)

where A' is —(NH—$(CH_2)_{x'}$)$_{y'}$—; —NH$(CH_2)_{x'}$—(O—$(CHR_1)_{r'}$)$_{w'}$—O—$(CH_2)_{x'}$—; or —NH—($(R_1CH)_{r'}$—O)$_{w'}$—$C_2H_4$—, A is —(($(CH_2)_x$—NH)$_y$; —$(CH_2)_x$—(O—$(CHR_1)_r$)$_w$—O—$(CH_2)_x$—NH—; or —(($R_1CH)_r$—O)$_w$—$C_2H_4$—NH—, $R_1$ is —H or —$CH_3$, Q is —NH— or —O—, p is 0 or 1, when p is 0 then Q is —O— and when p is 1 then Q is —NH—, r' is an integer from 2 to 4 or such as from 2 to 3, w' is an integer from 2 to 36 or such as from 32 to 36, x' is an integer from 2 to 6 or such as from 3 to 6, y' is an integer from 0 to 5 or such as from 2 to 5 or such as from 3 to 5, when y' is 0 then Q forms a chemical bond with H—, r is an integer from 2 to 4 or such as from 2 to 3, w is an integer from 2 to 36 or such as from 32 to 36, x is an integer from 2 to 6 or such as from 3 to 6, y is an integer from 0 to 5 or such as from 2 to 5 or such as from 3 to 5, when y is 0 then H— is bonded to the terminal nitrogen of —C(O)—NH—, t is an integer from 2 to 4 or such as 2 to 3, u is an integer from 1 to 5 or such as from 1 to 4 or such as from 1 to 2 or such as from 2 to 5 or such as from 3 to 5, and z is an integer from 1 to 13 or such as from 9 to 13 or such as from 1 to 3.

More typically such compounds include, but are not limited to:

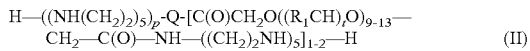
(II)

where $R_1$ is —H or —$CH_3$, Q is —NH— when p is 1 and —O— when p is 0 and t is an integer from 2 to 4 or such as from 2 to 3 or such as 2;

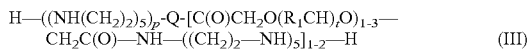
(III)

where $R_1$ is —H or —$CH_3$, Q is —NH— when p is 1 and —O— when p is 0 and t is an integer from 2 to 4 or such as from 2 to 3 or such as 2;

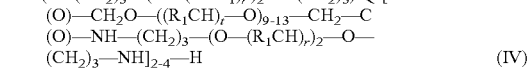
(IV)

where $R_1$ is —H or —$CH_3$,

Q is —NH— when p is 1 and —O— when p is 0, r and r' may be the same or different and are integers from 2 to 4 or such as 2 to 3 or such as 2, and t is an integer from 2 to 4 or such as from 2 to 3 or such as 2;

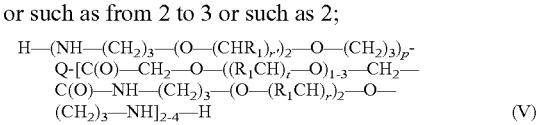
(V)

where $R_1$ is —H or —$CH_3$,

Q is —NH— when p is 1 and —O— when p is 0, r and r' may be the same or different and are integers from 2 to 4 or such as 2 to 3 or such as 2, and t is an integer from 2 to 4 or such as from 2 to 3 or such as 2;

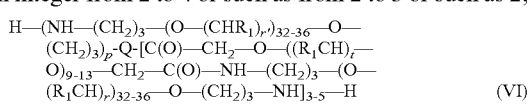
(VI)

where $R_1$ is —H or —CH$_3$,
Q is —NH— when p is 1 and —O— when p is 0, r and r' may be the same or different and are integers from 2 to 4 or such as from 2 to 3 or such as 2, and
t is an integer from 2 to 4 or such as from 2 to 3 or such as 2;

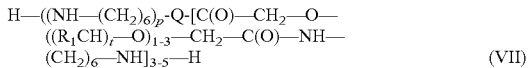

where $R_1$ is —H or —CH$_3$,
Q is —NH— when p is 1 and —O— when p is 0, and
t is an integer from 2 to 4 or such as from 2 to 3 or such as 2;

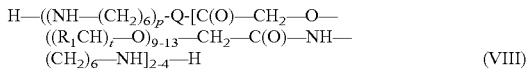

where $R_1$ is —H or —CH$_3$, Q is —NH— when p is 1 and —O— when p is 0, and
t is an integer from 2 to 4 or such as from 2 to 3 or such as 2;

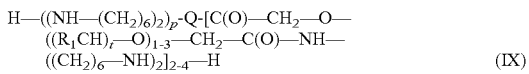

where $R_1$ is —H or —CH$_3$, Q is —NH— when p is 1 and —O— when p is 0, and t is an integer from 2 to 4 or such as from 2 to 3 or such as 2;

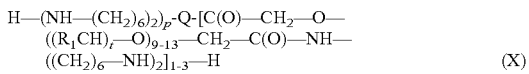

where $R_1$ is more typically —H or —CH$_3$,
Q is —NH— when p is 1 and —O— when p is 0, and
t is an integer from 2 to 4 or such as from 2 to 3 or such as 2;

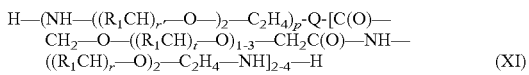

where $R_1$ is —H or —CH$_3$, Q is —NH— when p is 1 and —O— when p is 0, and
t is an integer from 2 to 4 or such as from 2 to 3 or such as 2;

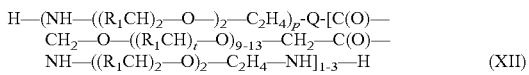

where $R_1$ is more typically —H or —CH$_3$,
Q is —NH— when p is 1 and —O— when p is 0, and
t is an integer from 2 to 4 or such as from 2 to 3 or such as 2; and

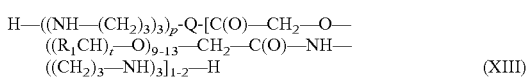

where $R_1$ is —H or —CH$_3$, Q is —NH— when p is 1 and —O— when p is 0, and
t is an integer from 2 to 4 or such as from 2 to 3 or such as 2.

Number average molecular weight of the compounds range from 250 and greater, or such as from 500 to 15,000, or such as from 900 to 10,000. The molecular weight of the compounds may be determined using any conventional method in the art.

The compounds of formulas (I)-(XIII) may be prepared from one or more polyethylene glycols and one or more polyalkoxylated diamines or alkylene triamines using conventional condensation reactions.

Polyethylene glycol diacids which may be used to prepare the compounds of formulas (I)-(XIII) include, but are not limited to, polyethylene glycol diacids having a formula:

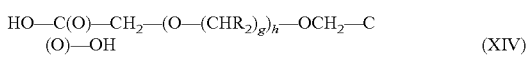

where g is an integer from 2 to 4,
h is an integer from 1 to 150, and $R_2$ is —H or —CH$_3$.
Such polyethylene glycol diacids have average number molecular weights ranging from 250 and greater.

Polyalkoxylated diamines used to make the compounds of formulas (I)-(XIII) include, but are not limited to, compounds having a formula:

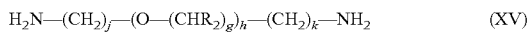

or

where g, h and $R_2$ are as defined above, j is an integer from 2 to 6, k is an integer from 0 to 6, and m is an integer from 6 to 10.

Alkylene triamines which may be used to make the compounds of formulas (I)-(XIII) include, but are not limited to, compounds having a formula:

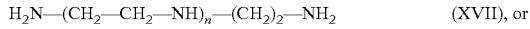

Any conventional method known in the art or published in the literature may be used to make the compounds of formulas (I)-(XIII). The starting materials may be obtained commercially or synthesized by methods known in the art and literature. Acid-terminated polyalkyleneglycols may be synthesized by oxidation of the polyalkyleneglycols as disclosed in U.S. Pat. No. 5,250,727 and U.S. Pat. No. 5,166,423 to produce carboxylic acids until all of the hydroxyl groups per molecule are oxidized to carboxylic acid groups to form a diacid. Acid-terminated polyalkyleneglycols may also be made by the well known Williamson ether synthesis by reacting polyalkyleneglycols with chloroacetic acid in the presence of a base.

Poly(ethyleneoxide) diamines may be prepared by the reaction of a bihydroxyl-initiator with ethylene oxide followed by conversion of the resulting terminal hydroxyl groups to amines Jeffamine™ brands of poly(alkyleneoxide) amines are available from Huntsman Performance chemicals, Houston, Tex., U.S.A., and propylamine-terminated polyethyleneoxide is available from ALDRICH.

In general, the reactants may range in weight ratios of 1:1 to 3:1. The condensation reaction proceeds under an inert gas atmosphere, such as under a N$_2$(g) atmosphere. Temperatures may range from 180° C. to 250° C. with pressures ranging from 10 mbar to atmospheric pressure. Progress of the reaction may be monitored by spectrographic methods, such as by NMR spectroscopy.

The amide compounds may be added to metal plating compositions to improve the performance of metal plating compositions. The amide compounds are included in metal plating compositions in amounts of 0.001 g/L to 5 g/L, or such as from 0.01 g/L to 1 g/L.

One or more sources of metal ions are included in metal plating compositions to plate metals. The one or more sources of metal ions provide metal ions which include, but are not limited to, copper, tin, nickel, gold, silver, palladium, platinum and indium. Alloys include, but are not limited to, binary and ternary alloys of the foregoing metals. Typically, metals chosen from copper, tin, nickel, gold, silver or indium are plated with the metal plating compositions. More typically, metals chosen from copper, tin, silver or indium are plated. Most typically, copper is plated.

Copper salts which may be used in the metal plating compositions include, but are not limited to, one or more of copper halides, copper sulfates, copper alkane sulfonate, copper alkanol sulfonate and copper citrate. Typically, copper sulfate, copper alkanol sulfonate or mixtures thereof are used in the plating compositions.

Tin salts which may be used in the metal plating compositions include, but are not limited to, one or more of tin sulfates, tin halides, tin alkane sulfonates such as tin methane sulfonate, tin ethane sulfonate, and tin propane sulfonate, tin aryl sulfonate such as tin phenyl sulfonate and tin toluene sulfonate, and tin alkanol sulfonate. Typically, tin sulfate or tin alkane sulfonate is used in the plating compositions.

Gold salts which may be used in the metal plating compositions include, but are not limited to, one or more of gold trichloride, gold tribromide, gold cyanide, potassium gold chloride, potassium gold cyanide, sodium gold chloride and sodium gold cyanide.

Silver salts which may be used in the metal plating compositions include, but are not limited to, one or more of silver nitrate, silver chloride, silver acetate and silver bromate. Typically, silver nitrate is used in the plating compositions.

Nickel salts which may be used in the metal plating compositions include, but are not limited to, one or more of nickel chloride, nickel acetate, nickel ammonium sulfate, and nickel sulfate.

Palladium salts which may be used in the metal plating compositions include, but are not limited to, one or more of palladium chloride, palladium nitrate, palladium potassium chloride and palladium potassium chloride.

Platinum salts which may be use include, but are not limited to, one or more of platinum tetrachloride, platinum sulfate and sodium chloroplatinate.

Indium salts which may be used include, but are not limited to, one or more of indium salts of alkane sulfonic acids and aromatic sulfonic acids, such as methanesulfonic acid, ethanesulfonic acid, butane sulfonic acid, benzenesulfonic acid and toluenesulfonic acid, salts of sulfamic acid, sulfate salts, chloride and bromide salts of indium, nitrate salts, hydroxide salts, indium oxides, fluoroborate salts, indium salts of carboxylic acids, such as citric acid, acetoacetic acid, glyoxylic acid, pyruvic acid, glycolic acid, malonic acid, hydroxamic acid, iminodiacetic acid, salicylic acid, glyceric acid, succinic acid, malic acid, tartaric acid, hydroxybutyric acid, indium salts of amino acids, such as arginine, aspartic acid, asparagine, glutamic acid, glycine, glutamine, leucine, lysine, threonine, isoleucine, and valine.

Additional metals which may be included in the metal plating compositions include, but are not limited to, one or more of bismuth, cobalt, chromium and zinc. Such metals may be included with one or more of the metals described above as alloying metals. Sources of bismuth ions include, but are not limited to, one or more of bismuth ammonium citrate and bismuth phosphate. Sources of cobalt ions include, but are not limited to, one or more of cobalt ammonium sulfate, cobalt acetate, cobalt sulfate and cobalt chloride. Sources of chromium ions include, but are not limited to, one or more of chromic acetate, chromic nitrate and chromic bromide. Sources of zinc ions include, but are not limited to, one or more of zinc bromate, zinc chloride, zinc nitrate and zinc sulfate.

Binary alloys which may be plated from the metal plating compositions include, but are not limited to, alloys of tin and copper, tin and bismuth, gold and silver, indium and bismuth, indium and zinc, and gold and cobalt. Typically, alloys of tin and copper are plated.

Ternary alloys which may be plated from the metal plating compositions include, but are not limited to, alloys of tin, silver and copper, and gold, silver and copper.

In general, the metal salts are included in the plating compositions such that metal ions range in concentrations from 0.01 g/L to 200 g/L, or such as from 0.5 g/L to 150 g/L, or such as from 1 g/L to 100 g/L, or such as from 5 g/L to 50 g/L. Typically, metal salts are included in amounts such that metal ion concentrations range from 0.01 to 100 g/L, more typically from 0.1 g/L to 60 g/L.

The metal plating compositions may also include one or more conventional diluents. Typically, the metal plating compositions are aqueous; however, conventional organic diluents may be used if desired. Optional conventional plating composition additives also may be included. Such additives include, but are not limited to, one or more of brighteners, suppressors, surfactants, inorganic acids, organic acids, brightener breakdown inhibition compounds, alkali metal salts, and pH adjusting compounds. Additional additives may be included in the metal plating compositions to tailor the performance of the metal plating for a particular substrate. Such additional additives may include, but are not limited to, other levelers and compounds which affect throwing power. Typically, when copper or one of its alloys is plated the plating composition includes one or more brighteners and one or more suppressors.

Brighteners include, but are not limited to, one or more of 3-mercapto-propylsulfonic acid sodium salt, 2-mercaptoethanesulfonic acid sodium salt, bissulfopropyl disulfide (BSDS), N,N-dimethyldithiocarbamic acid (3-sulfopropyl) ester sodium salt (DPS), (O-ethyldithiocarbonato)-S-(3-sulfopropyl)-ester potassium salt (OPX), 3-[(amino-iminomethyl)-thiol]-1-propanesulfonic acid (UPS), 3-(2-benzthiazolylthio)-1-propanesulfonic acid sodium salt (ZPS), the thiol of bissulfopropyl disulfide (MPS), sulfur compounds such as 3-(benzthiazoyl-2-thio)-propylsulfonic acid sodium salt, 3-mercaptopropane-1-sulfonic acid sodium salt, ethylenedithiodipropylsulfonic acid sodium salt, bis-(p-sulfophenyl)-disulfide disodium salt, bis-(ω-sulfobutyl)-disulfide disodium salt, bis-(ω-sulfohydroxypropyl)-disulfide disodium salt, bis-(ω-sulfopropyl)-disulfide disodium salt, bis-(ω-sulfopropyl)-sulfide disodium salt, methyl-(ω-sulfopropyl)-disulfide sodium salt, methyl-(ω-sulfopropyl)-trisulfide disodium salt, O-ethyl-dithiocarbonic acid-S-(ω-sulfopropyl)-ester, potassium salt thioglycoli acid, thiophosphoric acid-O-ethyl-bis-(ω-sulfpropyl)-ester disodium salt, and thiophosphoric acid-tris(ω-sulfopropyl)-ester trisodium salt.

Brighteners may be added to the metal plating compositions in conventional amounts. In general, brighteners are added in amounts of 1 ppb to 1 g/L, or such as from 10 ppb to 500 ppm.

Suppressors include, but are not limited to, one or more of oxygen containing high molecular weight compounds such as carboxymethylcellulose, nonylphenolpolyglycol ether, octandiolbis-(polyalkylene glycolether), octanolpolyalkylene glycolether, oleic acidpolyglycol ester, polyethylenepropylene glycol, polyethylene glycol, polyethylene glycoldimethylether, polyoxypropylene glycol, polypropylene glycol, polyvinylalcohol, stearic acidpolyglycol ester, and stearyl alcoholpolyglycol ether. Typically poly(alkoxylated)glycols are used. Such suppressors may be included in the metal plating formulations in conventional amounts, such as from 0.01 g/L to 10 g/L or such as from 0.5 g/L to 5 g/L.

One or more conventional surfactants may be used. Typically, surfactants include, but are not limited to, nonionic surfactants such as alkyl phenoxy polyethoxyethanols. Other suitable surfactants containing multiple oxyethylene groups also may be used. Such surfactants include compounds of polyoxyethylene polymers having from as many as 20 to 150 repeating units. Such compounds also may perform as suppressors. Also included in the class of polymers are both block and random copolymers of polyoxyethylene (EO) and polyoxypropylene (PO). Surfactants may be added in conventional amounts, such as from 0.05 g/L to 20 g/L or such as from 0.5 g/L to 5 g/L.

Conventional levelers include, but are not limited to, one or more of alkylated polyalkyleneimines and organic sulfo sulfonates. Examples of such compounds include, 4-mercaptopyridine, 2-mercaptothiazoline, ethylene thiourea, thiourea, 1-(2-hydroxyethyl)-2-imidazolidinethion (HIT) and alkylated polyalkyleneimines. Such levelers are included in conventional amounts. Typically, such levelers are included in amounts of 1 ppb to 1 g/L, or such as from 10 ppb to 500 ppm.

One or more inorganic and organic acids are included in the metal plating compositions to increase the solution conductivity of the matrix and also to adjust the pH of the plating composition. Inorganic acids include, but are not limited to, sulfuric acid, hydrochloric acid, nitric acid and phosphoric acid. Organic acids include, but are not limited to, alkane sulfonic acids, such a methane sulfonic acid. Acids are included in the plating compositions in conventional amounts.

Alkali metal salts which may be included in the plating compositions include, but are not limited to, sodium and potassium salts of halogens, such as chloride, fluoride and bromide. Typically chloride is used. Such alkali metal salts are used in conventional amounts.

One or more brightener breakdown inhibiting compounds may be included in the plating compositions. Brightener breakdown inhibiting compounds include any compound which is compatible with the other components of the compositions and prevents or at least inhibits the breakdown of brighteners in the plating compositions. Typically, such compounds are included in metal plating baths for electroplating with insoluble anodes. Such compounds include, but are not limited to aldehydes such as 2,3,4-trihydroxybenzaldehyde, 3-hydroxybenzaldehyde, 3,4,5-trihydroxybenzaldehyde, 2,4-dihydroxybenzaldehyde, 4-hydroxy-3-methoxy cinnamaldehyde, 3,4,5-trihydroxybenzaldehyde monohydrate, syringealdehyde, 2,5-dihydroxybenzaldehyde, 2,4,5-trihydroxybenzaldehyde, 3,5-hydroxybenzaldehyde, 3,4-dihydroxybenzaldehyde, 4-hydroxybenzaldehyde, 4-carboxybenzaldehyde, 2-chloro-4-hydroxybenzaldehyde, and 3-furanaldehyde. Other aldehydes include, but are not limited to, pyridine carboxaldehyde, benzaldehyde, naphthaldehyde, biphenyl aldehyde, anthracene aldehyde, phenanthracene aldehyde, and 2-formyl phenoxy acetic acid.

Hydroxylamines which may function as brightener breakdown inhibitors include, but are not limited to, hydroxylamine sulfate, hydroxylamine nitrate and hydroxylamine chloride. Typically, hydroxylamine sulfate or hydroxylamine nitrate are used.

Various alcohols also may be used as brightener breakdown inhibitors. Such alcohols include, but are not limited to, alkyl, alkenyl and alkynyl alcohols, unbranched and branched, as well as aromatic alcohols, non-aromatic cyclic alcohols and heterocyclic alcohols. Such alcohols include crotyl alcohol, 2-methylene-1,3-propanediol, 3-butene-1-ol, and 1,4-anhydro-erythritol. Other alcohols include naphthalene derivatives such as 1,2-dihydroxynaphthalene, 1,3-dihydroxynaphthalene, 2,3-dihydroxynaphthalene, 2,4-dihydroxynaphthalene, 2,7-dihydroxynaphthalene, 2,6-dihydroxynaphthalene, 4,5-dihydroxynaphthalene-2,7-disulfonic acid disodium salt, 6,7-dihydroxynaphthalene-2,7-disulfonic acid, 6-hydroxy-2-naphthalene sulfonic acid, 4-amino-5-hydroxy-2,7-naphthalene disulfonic acid monosodium salt, 1,5-dihydroxy-1,2,3,4-tetrahydra-naphthalene, 2,6-dihydroxynaphthalene, 1,5-dihydroxynaphthalene, 1-naphthol-3,6-disulfonic acid disodium salt hydrate, decahydro-2-naphthol, 1,2,3,4-tetrahydro-1-naphthol, 2-naphthalene methanol, 1,6-dihydroxynaphthalene, 6,7-dihydroxy-2-naphthalene sulfonic acid hemihydrate, and 4-hydroxy-1-naphthalene sulfonic acid sodium salt. Preferred aromatic alcohols include 5-methoxyresorcinol, 4-chlororesorcinol, 2-nitroresorcinol, 2-allyl phenol, 1,2,4-benzenetriol, isoeugenol, $\alpha,\alpha,\alpha$-trifluoro-m-cresol, 4-tert-butyl catechol, 3-hydroxy-1-benzyl alcohol, 4-hydroxybenzyl alcohol, phloroglucinol dihydrate and anhydride, olivetol, and 3-chlorophenol.

Examples of other suitable alcohols include 1,2-benzenedimethanol, 1,3-benzenedimethanol, 4-aminophenol, 4-methoxyphenol, 4-ethylresorcinol, hydroquinone, chloroquinone, hydroquinone sulfonic acid potassium salt, 4-(methylthio)-benzyl alcohol, benzyl alcohol, coniferyl alcohol, 3-methoxycatechol, 4-mercapto-phenol, 4,4'-thiodiphenol, 3-methoxy phenol, phenol, cresol, and orcinol monohydrate. Other preferred compounds include, but are not limited to, 2',4',6'-trihydroxyacetophenone monohydrate, 2,5-dihydroxy-1,4-benzoquinone, and tetrahydroxy-1,4-quinonehydrate.

Heterocyclic compounds include saturated lactones or lactones having one or more double bonds. Such lactones include ascorbic acid and $\alpha$-hydroxy-$\gamma$-butyrolactone. Also included are the metal salts of such lactones such as the sodium, potassium and iron salts. Examples of other heterocyclic compounds include 2-hydroxybenzofuran, 5,6-dihydro-4-hydroxy-6-methyl-2H-pyran-2-one, 2-hydroxybenzofuran, naringin hydrate, sesamol, 2,4-dihydroxy-6-methyl pyrimidine, and 1,2,4-triazolo(1,5-A)-pyrimidine.

Examples of other suitable compounds include 3-furanmethanol, 2,4,5-trihydroxy-pyrimidine, 5,6-isopropylidene ascorbic acid, and dehydroascorbic acid.

Organic acids also may function as brightener breakdown inhibitors. Such acids include, but are not limited to, one or more of 2,6-dihydroxybenzoic acid, 4-hydroxybenzoic acid resorcinol, 2,3-dihydroxybenzoic acid, 2,4-dihydroxybenzoic acid, 2,4,6-trihydroxybenzoic acid, 2,3,4-trihydroxybenzoic acid, methyl-3,4,5-trihydroxybenzoate, methyl-2,4-dihydroxybenzoate, 4-hydroxymandelic acid monohydrate, 3-(phenylthio)acetic acid, 4-hydroxybenzene sulfonic acid, gallic acid, 4-vinylbenzoic acid, 3,4-dihydroxy cinnamic acid, 4-methoxy cinnamic acid, 2-hydroxy cinnamic acid, phthalic acid, trans-3-furanyl acrylic acid, vinyl acetic acid, and sulfanilic acid. Also included are acid anhydrides such as phthalic anhydride.

Other compounds which may function as brightener break down inhibitors include, but are not limited to, methyl sulfoxide, methyl sulfone, tetramethylene sulfoxide, thioglycolic acid, 2 (5H) thiophenone, 1,4-dithiane, trans-1,2-dithiane, 4,5-diol, tetrahydrothiophen-3-one, 3-thiophenemethanol, 1,3,5-trithiane, 3-thiophenacetic acid, thiotetronic acid, thioctic acid, crown ethers, crown thioethers, tetrapyrids, ethane thiosulfonate, (2-sulfonatoethyl) methane sulfonate, carboxyethylmethane thiosulfonate, 2-hydroxyethylmethane thiosulfate, 1,4-butanediyl bismethane thiosulfonate, 1,2-ethanediylbismethane thiosulfonate, 1,3-propanediyl methane thiosulfonate, (3-sulfonatopropyl)methane thiosulfonate, propylmethane thiosulfonate, p-tolyldisulfoxide, p-tolyldisulfone, bis(phenylsulfonyl) sulfide, isopropyl sulfonyl chloride, 4-(chlorosulfonyl)benzoic acid, dipropyltrisulfide, dimethyltrisulfide, dimethyltetrasulfide, bis(3-triethoxysilyl)propyltetrasulfide, phenyl vinyl sulfone, 4-hydroxy-benzene sulfonic acid, 1,4,7,10,13,16-hexamethyl-1,4,7,10,13,16-hexaazacyclooctadecane, 1,4,7,10- tetra-p-tosyl-1,4,7,10-tetraazacyclododecane, and 1,4,10,13-tetraoxa-7,16-diazacyclooctadecane.

Brightener breakdown inhibitors are included in the plating compositions in amounts of 0.001 g/L to 100 g/L. Typically, such compounds are included in amounts of 0.01 g/L to 20 g/L.

The measured pH of the metal plating compositions may range from −1 to 14, or such as from −1 to 8. Typically, the measured pH of the plating compositions ranges from −1 to 5, more typically, from −1 to 3. Conventional buffering compounds may be included to control the pH of the compositions.

The metal plating compositions may be used to plate a metal or metal alloy on a substrate by any method known in the art and literature. Typically, the metal or metal alloy is electroplated using conventional electroplating processes with conventional apparatus. A soluble or insoluble anode may be used with the electroplating compositions.

Pulse plating or direct current (DC) plating or a combination of DC and pulse plating may be used. Such plating processes are known in the art. Current densities and electrode surface potentials may vary depending on the specific substrate to be plated. Generally, anode and cathode current densities may vary from 0.01 to 15 A/dm$^2$. Low speed plating ranges from 0.1 A/dm$^2$ to 3 A/dm$^2$. High speed plating ranges from 3 A/dm$^2$ and higher, typically from 3 A/dm$^2$ to 15 A/dm$^2$. Plating baths are maintained in a temperature range of from 20° C. to 110° C., or such as from 20° C. to 50° C. Plating temperatures may vary depending on the metal to be plated.

Including the amides in metal plating compositions provide at least improved leveling performance over many conventional metal plating compositions. Such metal plating compositions may be used in metal plating in the manufacture of electrical devices such as printed wiring boards, including the plating of through-holes and vias, integrated circuits, electrical contact surfaces and connectors, electrolytic foil, silicon wafers for microchip applications, semi-conductors and semi-conductor packaging, lead frames, optoelectronics and optoelectronic packaging, and solder bumps. Additionally, the metal plating compositions may be used for metal plating decorative articles such as jewelry, furniture fittings, automobile parts, and sanitary appliances.

The following examples are provided to better illustrate the invention, but are not intended to limit the scope of the invention.

EXAMPLE 1

24 g of poly(ethylene glycol) bis(carboxymethyl) ether 600 with a number average molecular weight of 600 from Fluka (Chemical company Buchs, Switzerland) is reacted for 6 hours at 190-200° C. with 19 g pentaethylene-hexamine from ALDRICH at a molar ratio of 1:1.7 in a round bottom flask with a short glass tube, distillation head, Liebig condenser and receiver flask under constant inert gas supply. Water is distilled out of the flask. The reaction liquid is heated using a condenser and receiver flask at 200° C. and 15 mbar. The remaining product is dissolved in water and extracted with ether. The water phase is dried by evaporation to yield a polyamidoamine having a formula:

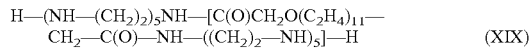  (XIX)

The structure is determined using carbon 13 and hydrogen 1 NMR spectroscopy. The number average molecular weight is 1050 as determined by SEC.

EXAMPLE 2

13 g polyethyleneglycol-bis(carboxymethylether) 250 from ALDRICH with a number average molecular weight of 250 is reacted as described in Example 1 for 6 hours at 190-200° C. with 23 g of pentaethylene-hexamine at a molar ration of 1:2. The reaction is completed at 200° C. at 30 mbar. The structure is determined using NMR spectroscopy.

The structure of the polyamidoamine is then determined using carbon 13 and hydrogen 1 NMR spectroscopy. The polyamidoamine has the following formula:

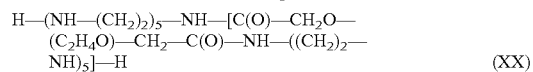  (XX)

The number average molecular weight is 600-650 as determined by SEC.

EXAMPLE 3

18 g of polyethyleneglycol bis(carboxymethylehter) 600 is reacted with 7 g of 4,7,10-trioxa-1,13-tridecanediamine from ALDRICH for 2 hours at 190-240° C. as described under Example 1. The molar ratio of the reactants is 1:1.1. The reaction water is distilled out and the product has a formula:

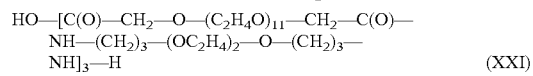  (XXI)

The formula is determined using NMR spectroscopy. The number average molecular weight is 2430 as determined by SEC.

EXAMPLE 4

10 g of polyethyleneglycol bis(carboxylmethylehter) 250 is reacted with 18 g of 4,7,10-trioxa-1,13-tridecanediamine for 1 hour at 180-220° C. as described in Example 1 at a molar ratio of 1:2. The reaction is completed by heating to 220-250° C. at 30 mbar for 4 hours and after a further 3 hours at 250° C. at 1 mbar. The structure of the reaction product is determined by NMR spectroscopy and has the following structure:

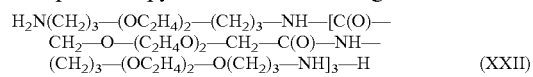  (XXII)

The number average molecular weight is 1600 as determined by SEC.

EXAMPLE 5

6 g of polyethyleneglycol bis(carboxymethylether) 600 is reacted for 2 hours at 230-240° C. with 16 g of O,O'-bis(3-aminopropyl)polyethylene glycol 1500 from ALDRICH at a molar ratio of 1:1. The reaction apparatus is the same as described in Example 1. The reaction water is distilled out to yield a brownish solid. The product is dissolved in water and filtrated through an active charcoal filter and then fine filtrated. The product is dried by evaporation. The structure of the reaction product is determined by NMR spectroscopy and has the following structure:

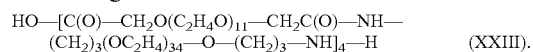  (XXIII).

The number average molecular weight is 8800 as determined by SEC.

EXAMPLE 6

24 g of polyethyleneglycol bis(carboxylmethylether) 250 is reacted for 5 hours at 200° C. with 18 g of 1,6-diaminohexane from ALDRICH at a molar ratio of 1:1.6. The apparatus is the same as described in Example 1. The reaction water is distilled out with some educt. The educt is dissolved in water. The water is evaporated and the educt is distilled out at 210-220° C. at 30 mbar over 3 hours. A yellowish wax product is obtained. The structure of the product is determined by NMR spectroscopy and has the following structure:

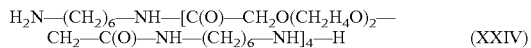
(XXIV)

The molecular weight as determined by SEC 1300.

EXAMPLE 7

24 g of polyethyleneglycol-bis(carboxymethylether) 600 are reacted for 3.5 hours at 200-210° C. with 9.5 g of 1,6-diaminohexane at a molar ratio of 1:2. The reaction is carried out using the same apparatus as described in Example 1 above. The reaction water is distilled out with some amine. Further amine is removed at 200-210° C. at 30 mbar to yield a product having a formula:

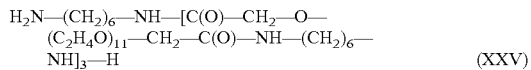
(XXV)

The number average molecular weight is determined to be 2200 by SEC.

EXAMPLE 8

12.5 g of polyethyleneglycol-bis(carboxymethylether) 250 are reacted with 19 g of bis(hexamethylene)triamine for 4.5 hours at 200-230° C. at a molar ratio of 1:1.8. The reaction water is distilled out. Heating is continued at 240° C. for 5 hours and then over 1 hour at 250° C. at 30 mbar leaving a syrupy oil which solidified upon standing at room temperature. The oil is soluble in water as a turbid solution and as a clear solution upon addition of concentrated laboratory grade sulfuric acid. The polycondensate has the following formula:

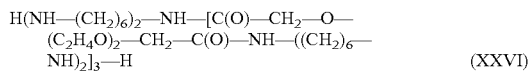
(XXVI)

The number average molecular weight is 1400.

EXAMPLE 9

24 g of polyethyleneglycol-bis(carboxymethylether) 600 is reacted with 15 g of bis(hexamethylene)triamine for 1 hour at 200-210° C. at a molar ratio of 1:1.7. The reaction water is distilled out. Heating is continued at 240° C. for 5 hours and finally at 240° C. at 30 mbar over 5 hours. The product has the following formula:

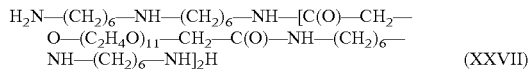
(XXVII)

The number average molecular weight is 1800.

EXAMPLE 10

12.5 g of polyethyleneglycol-bis(carboxymethylether) 250 are reacted with 15 g of 2,2'-ethylenedioxybisethylamine for 2.5 hours at 180-185° C. and for 1.5 hours at 200-210° C. at a molar ratio of 1:2. The reaction water is distilled out. After heating for an additional 2 hours at 220° C. at 30 mbar, an oil is obtained. The oil product has a formula:

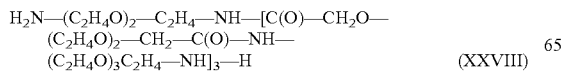
(XXVIII)

The number average molecular weight is 1150.

EXAMPLE 11

21 g of polyethyleneglycol-bis(carboxymethylether) 600 is reacted with 10 g of 2,2'-ethylenedioxybisethylamine for 4 hours at 200-210° C. at a molar ratio of 1:2. The reaction water is distilled out. After heating for an additional 2 hours at 220° C. at 30 mbar an oil is obtained. The oil is dissolved in water and treated with active charcoal. It is then fine filtrated, dried and lyophilized to yield brownish syrupy oil. The product has a formula:

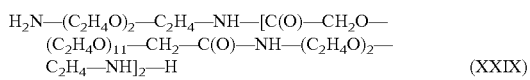
(XXIX)

The number average molecular weight is 1600.

EXAMPLE 12

16 g of polyethyleneglycol-bis(carboxymethylether) 600 is reacted with 10 g of N,N'-bis-(3-aminopropyl)-1,3-propanediamine at a molar ratio of 1:2 for 2.5 hours at 180-190° C. and then for 1.5 hours at 200-220° C. The reaction water is distilled out. Further heating is then carried out at 250° C. at 15 mbar. A black oil remained in the reaction vessel. The oil is dissolved in water and treated with active charcoal. Orange oil is obtained after filtration and drying by evaporation. The product has a formula:

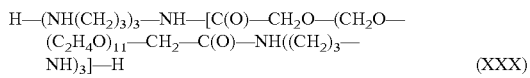
(XXX)

The molecular weight of the product is 960.

EXAMPLE 13

A stock solution of an aqueous copper plating composition is prepared with the following concentrations of materials: 80 g/L copper sulfate pentahydrate, 225 g/L sulfuric acid and hydrochloric acid in sufficient amount to provide 60 mg/L chloride ions. Aliquots are taken from the stock solution to make fourteen 1400 ml solutions containing a brightener and a suppressor. Twelve of the solutions also include a compound from Examples 1-12. The table below discloses the fourteen formulations.

TABLE 1

| SOLUTION | Compound | Brightener | Suppressor |
|---|---|---|---|
| 1 | Example 1 | BSDS | Copolymers of EO/PO |
| 2 | Example 2 | DPS | Carboxymethylcellulose |
| 3 | Example 3 | ZPS | Polyethylene glycol |
| 4 | Example 4 | OPX | Polyvinyl alcohol |
| 5 | Example 5 | 2-mercapto-ethansulfonic acid | Oleic acidopolyglycol ester |
| 6 | Example 6 | UPS | Polyethylene glycol |
| 7 | Example 7 | BSDS | Nonylphenolpolyglycol ether |
| 8 | Example 8 | 3-mercaptopropane-1-sulfonic acid | Polyvinyl alcohol |
| 9 | Example 9 | UPS | Polyethylene glycol dimethyl ether |
| 10 | Example 10 | MPS | Carboxymethylcellulose |
| 11 | Example 11 | Potassium salt of thioglycolic acid | Polyethylene glycol |

TABLE 1-continued

| SOLUTION | Compound | Brightener | Suppressor |
|---|---|---|---|
| 12 | Example 12 | Ethylenedithio-propylsulfonic acid | Polyethylenepropylene glycol |
| 13 | 0 (control) | BSDS | Copolymer of EO/PO |
| 14 | 0 (control) | MPS | Polyethylene glycol |

The compounds from Examples 1-12 are included in the samples in amounts of 1 g/L. The brighteners are included in amounts of 0.01 g/L and the suppressors are included in amounts of 0.5 g/L. Each 1400 ml aliquot of the aqueous copper plating composition is then added to a conventional Haring cell. Phosphorized copper anodes are immersed in either side of the Haring cell and are electrically connected to a conventional rectifier. A double sided copper clad panel (0.16 cm thick, 5 cm×15 cm) is then immersed in the center of the Haring cell, and the panels are then plated for 50 minutes at 3 A/dm$^2$ with air agitation. Electroplating is done at room temperature.

After 50 minutes the panels are removed, immersed in an anti-tarnish solution of 20% by volume aqueous Antitarnish™ 7130 (obtainable from Rohm and Haas electronic materials, Marlborough, Mass.) and air-dried with a blower. The copper plating on the panels which are plated in the solutions with the compounds of Examples 1-12 are expected to be bright and smooth. Additionally, no observable defects on the panels, such as nodules, step plating and fingerprints are expected to be observable. In contrast, the panels which are plated with the solutions without the compounds of Examples 1-12 are expected to be hazy.

The procedure above is repeated with three new sets of panels. One set is plated at 1 A/dm$^2$ for 150 minutes, the second set is plated at 2 A/dm$^2$ for 70 minutes and the third set is plated at 4 A/dm$^2$ for 35 minutes. All of the panels electroplated with samples containing the compounds of Examples 1-12 are expected to have bright and smooth copper plating with no observable defects. In contrast, the samples which do not include the compounds of Examples 1-12 are expected to be hazy.

EXAMPLE 14

A copper electroplating stock solution as described in Example 13 is prepared. Fifty 1400 ml aliquots are taken from the stock solution to make fifty separate test solutions. The composition of each test solution is disclosed in Table 2 below.

TABLE 2

| SAMPLES | Compounds | Brightener | Suppressor |
|---|---|---|---|
| 1-4 | Example 1 | BSDS | Copolymer of EO/PO |
| 5-8 | Example 2 | UPS | Polyethylene glycol |
| 9-12 | Example 3 | MPS | Polyvinyl alcohol |
| 13-16 | Example 4 | DPS | Polyethylene glycol |
| 17-20 | Example 5 | OPX | Carboxymethylcellulose |
| 21-24 | Example 6 | ZPS | Copolymer of EO/PO |
| 25-28 | Example 7 | BSDS | Polyethylene glycol |
| 29-32 | Example 8 | OPX | Polyvinyl alcohol |
| 33-36 | Example 9 | MPS | Polyethylene glycol |
| 37-40 | Example 10 | BSDS | Carboxymethylcellulose |
| 41-44 | Example 11 | ZPS | Polyvinyl alcohol |
| 45-48 | Example 12 | DPS | Copolymer of EO/PO |
| 49 | 0 (control) | BSDS | Polyethylene glycol |
| 50 | 0 (control) | MPS | Polyethylene glycol |

Each sample includes brighteners in amounts of 1 g/L and the suppressors in amounts of 5 g/L. The amounts of the compounds from Examples 1-12 in each sample are varied. Samples 1-4 include the compound from Example 1 in amounts of 0.001 g/L, 0.01 g/L, 0.5 g/L and 1 g/L, respectively. Samples 5-8 include the compound from Example 2 in amounts of 0.005 g/L, 0.01 g/L, 0.5 g/L and 1 g/L, respectively. Samples 9-12 include the compound from Example 3 in amounts of 0.05 g/L, 0.25 g/L, 0.5 g/L and 1 g/L, respectively. Samples 13-16 include the compound from Example 4 in amounts of 0.01 g/L, 0.25 g/L, 0.5 g/L and 1 g/L, respectively. Samples 17-20 include the compound from Example 5 in amounts of 0.001 g/L, 0.05 g/L, 0.1 g/L and 1 g/L, respectively. Samples 21-24 include the compound from Example 6 in amounts of 0.001 g/L, 0.01 g/L, 0.5 g/L and 1 g/L, respectively. Samples 25-28 include the compound from Example 7 in amounts of 0.01 g/L, 0.25 g/L, 0.5 g/L and 1 g/L, respectively. Samples 29-32 include the compound of Example 8 in amounts of 0.001 g/L, 0.01 g/L, 0.1 g/L and 1 g/L, respectively. Samples 33-36 include the compound of Example 9 in amounts of 0.05 g/L, 0.25 g/L, 0.75 g/L and 1 g/L, respectively. Samples 37-40 include the compound of Example 10 in amounts of 0.05 g/L, 0.25 g/L, 0.5 g/L and 0.75 g/L, respectively. Samples 41-44 include the compound from Example 11 in amounts of 0.05 g/L, 0.1 g/L, 0.5 g/L and 1 g/L, respectively. Samples 45-48 include the compound of Example 12 in amounts of 0.01 g/L, 0.5 g/L, 0/75 g/L and 1 g/L, respectively.

Each sample is placed in a Haring cell and phosphorized copper anodes are immersed in either side of each Haring cell. The cells are electrically connected to a conventional rectifier. A double sided copper clad panel (0.16 cm thick, 5 cm×15 cm) with multiple 0.2 mm diameter through-holes are placed in the center of each haring cell. Each panel is electroplated for 50 minutes at 3 A/dm$^2$ with air agitation. Electroplating is done at room temperature. After electroplating is completed the panels are removed from the Hering cells and cross-sectioned to inspect the thickness of the copper plating of the through-holes. The through-holes are inspected using an optical microscope at 200× magnification. The through-holes with the samples containing the compounds of Examples 1-12 are expected to show improved throwing power by having thicker and more uniform copper layers in the center of the through holes than the two control samples.

EXAMPLE 15

An aqueous tin plating composition which includes 20 g/L of tin ions from tin sulfate, 40 g/L of sulfuric acid, 0.5 g/L of an ethylene oxide/propylene oxide copolymer having an average molecular weight of 2200, 10 ml/L of sulfated alkyl ethoxylate (TRITON™ QS-15) and 0.1 g/L of compound XIX of Example 1 is placed in a Haring cell as described in Example 13. The pH of the tin plating composition is less than 1 and the temperature is 30° C. The substrate is a bronze coupon 5 cm×15 cm. Tin electroplating is done at 3 A/dm$^2$ for 50 minutes. The tin layer is expected to be smooth and free of any observable defects.

EXAMPLE 16

An aqueous tin/copper alloy plating composition which includes 30 g/L of tin ions from tin sulfate, 20 g/L of copper ions from copper sulfate pentahydrate, 50 g/L of sulfuric acid, 1 g/L of an ethylene oxide/propylene oxide copolymer having an average molecular weight of 3000, 20 ml/L of a polyethoxylated amine (JEFFAMINE™ T-403, available from Huntsman Corporation) and 0.1 g/L of compound XX of Example 2 is placed in a Haring cell as described in Example 13. The pH of the tin/copper plating composition is less than 1 and the temperature is 30° C. The substrate is a bronze coupon 5 cm×15 cm. Tin/copper electroplating is done at 4 A/dm² for 35 minutes. The tin/copper alloy layer is expected to be smooth and free of any observable defects.

EXAMPLE 17

An aqueous tin/bismuth alloy plating composition which includes 25 g/l of tin ions from tin sulfate, 10 g/L of bismuth ions from bismuth trichloride, 90 g/L of sulfuric acid, 2 g/L of an ethylene oxide/propylene oxide copolymer with an average molecular weight of 2500, 10 ml/L of sulfated alkyl ethoxylate (TRITON™ QS-15) and 0.1 g/L of compound XXI of Example 3 is placed in a Haring cell as described in Example 13. The pH of the tin/bismuth composition is less than 1 and the temperature is at 30° C. The substrate is a bronze coupon 5 cm×15 cm. Tin/bismuth electroplating is done at 2 A/dm² for 60 minutes. The tin/bismuth alloy layer is expected to be smooth and free of any observable defects.

EXAMPLE 18

An aqueous tin/indium alloy plating composition which includes 35 g/L of tin ions from tin sulfate, 5 g/L of indium ions from indium trichloride, 50 g/L of sulfuric acid, 1 g/L of an ethylene oxide/propylene oxide copolymer with an average molecular weight of 5000, 10 ml/L of a sulfated alkyl ethoxylate (TRITON™ QS-15), and 0.1 g/L of XXII of Example 4 is placed in a Haring cell as described in Example 13. The pH of the tin/indium composition is less than 1 and the temperature is at 30° C. The substrate is a bronze coupon 5 cm×15 cm. Tin/indium electroplating is done at 1 A/dm² for 100 minutes. The tin/indium alloy layer is expected to be smooth and free of any observable defects.

EXAMPLE 19

An aqueous tin/silver/copper alloy plating composition which includes 40 g/L tin ions from tin methane sulfonate, 1 g/L silver ions from silver methane sulfonate, 1 g/L copper from copper methane sulfonate, 90 g/L methane sulfonic acid, 2 g/L ethoxylated bis phenol, 4 g/L 1-allyl-2-thiourea and 0.1 g/L of compound XXIII of Example 5 is placed in a Haring cell as described in Example 13. The pH of the tin/silver/copper composition is 1 and the temperature is at 30° C. The substrate is a bonze coupon 5 cm×15 cm. Tin/silver/copper electroplating is done at 2 A/dm² for 100 minutes. The tin/silver/copper alloy layer is expected to be smooth and free of any observable defects.

EXAMPLE 20

The metal plating process described in Example 15 is repeated with the same type of tin plating composition and metal plating parameters except that the compound is compound XXIV of Example 6. The tin layers deposited on the panels are expected to be smooth and without observable defects.

EXAMPLE 21

The metal plating process described in Example 15 is repeated with the same type of tin plating composition and metal plating parameters except that the compound is compound XXV of Example 7. The tin layers deposited on the panels are expected to be smooth and without observable defects.

EXAMPLE 22

The metal plating process described in Example 16 is repeated with the same type of tin/copper plating composition and metal plating parameters except that the compound is compound XXVI of Example 8. The tin/copper layers on the panels are expected to be smooth and without observable defects.

EXAMPLE 23

The metal plating process described in Example 16 is repeated with the same type of tin/copper plating composition and metal plating parameters except that the compound is compound XXVII of Example 9. The tin/copper layers on the panels are expected to be smooth and without observable defects.

EXAMPLE 24

The metal plating process described in Example 17 is repeated with same type of tin/bismuth plating composition and metal plating parameters except the compound is compound XXVIII of Example 10. The tin/bismuth layers on the panels are expected to be smooth and without observable defects.

EXAMPLE 25

The metal plating process described in Example 17 is repeated with the same type of tin/bismuth plating composition and metal plating parameters except that the compound is compound XXIX of Example 11. The tin/bismuth layers on the panels are expected to be smooth and without observable defects.

EXAMPLE 26

The metal plating process described in Example 16 is repeated with the same type of tin/copper plating composition and metal plating parameters except that the compound is compound XXX of Example 12. The tin/copper layers on the panels are expected to be smooth and without observable defects.

EXAMPLE 27

A series of experiments was performed to compare the effect of the leveler component on the thickness of the deposited copper electroplated from a copper plating bath. In each case below an individual leveler (or, in some cases, no leveler) was added to a copper plating bath, a panel was then electroplated, the panel was then processed, and the thickness of the electroplated copper deposit was then measured both on the surface of the panel as well as in the center of the through holes drilled into the panel. After the plating experiment, the solution was discarded and fresh stock solution was used in the next experiment.

A stock solution of an aqueous copper plating bath was prepared with the following concentration of inorganic materials: 75 g/L copper sulfate pentahydrate, 190 g/L sulfuric acid, and hydrochloric acid in sufficient amount to provide 60 mg/L chloride ions. 3 mL/L of Rohm and Haas Electronic Materials' Copper Gleam™ ST-901A additive (brightener) and 1.5 g/L of a poly(alkoxylated)glycol (suppressor) were added to the stock solution. 1500 mL of this solution was then added to a Haring cell. Phosphorized copper slabs were immersed at either side of the Haring cell, and were used as anodes during the plating cycle. A double sided copper clad panel (1.6 mm thick, 5 cm×10 cm plating area) was placed in the center of the Haring cell, and served as the cathode during the plating cycle. Air agitation was used throughout the plating experiment. Through holes have been drilled into the panel, and the panel was processed such that a thin, but adherent, layer of copper (20-25 mm) was chemically deposited onto the entire exposed surface of the panel, including the through holes. An amount of leveler or no leveler was then added to the solution in the Haring cell. Copper was then electroplated at a current density of 3 A/dm² for 50 minutes. The panel was then rinsed in deionized water. An area of the board was then processed such that the thickness of the copper plated on the surface and in the center of the through holes (0.32 mm diameter) was measured. The measure of the copper thickness in the center of the through holes was an indication of the throwing power of the bath, or the ability of a particular plating bath to electroplate copper inside the through holes. A thicker deposit measured in the through hole indicated a higher throwing power, and was more desirable. The measured copper thickness from plating baths containing various levelers is shown in Table 3.

TABLE 3

| Structure number | Leveler concentration, g/L | Copper thickness, mil |
|---|---|---|
| No leveler | 0 | 0.56 |
| XIX | 0.005 | 0.77 |
| XIX | 0.025 | 1.00 |
| XX | 0.005 | 1.00 |
| XX | 0.010 | 1.00 |
| XX | 0.025 | 0.98 |
| XXI | 0.010 | 0.69 |
| XXI | 0.150 | 0.65 |
| XXIII | 0.010 | 0.61 |
| XXIII | 0.150 | 0.71 |
| XIV | 0.001 | 0.81 |

TABLE 3-continued

| Structure number | Leveler concentration, g/L | Copper thickness, mil |
|---|---|---|
| XIV | 0.010 | 0.75 |
| XIV | 0.025 | 0.95 |
| XIV | 0.050 | 0.98 |
| XXV | 0.010 | 0.68 |
| XXV | 0.025 | 0.65 |

All levelers showed an improvement in the thickness of the copper plated at the center of the through hole compared to plating baths that contained no leveler.

What is claimed is:

1. Compounds having a formula:

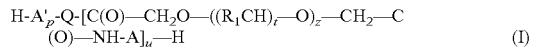

$$\text{H-A'}_p\text{-Q-[C(O)—CH}_2\text{O—((R}_1\text{CH)}_{r'}\text{—O)}_z\text{—CH}_2\text{—C(O)—NH-A]}_u\text{—H} \quad (I)$$

where A' is —(NH—(CH$_2$)$_{x'}$)$_{y'}$—; —NH(CH$_2$)$_{x'}$—(O—(CHR$_1$)$_{r'}$)$_{w'}$—O—(CH$_2$)$_{x'}$—; or —NH—((R$_1$CH)$_{r'}$—O)$_{w'}$—C$_2$H$_4$—;

A is —((CH$_2$)$_x$—NH)$_y$—; —(CH$_2$)$_x$—(O—(CHR$_1$)$_r$)$_w$—O—(CH$_2$)$_x$—NH—; or —((R$_1$CH)$_r$—O)$_w$—C$_2$H$_4$—NH—;

R$_1$ is —H or —CH$_3$,

Q is —NH— when p=1 or —O— when p=0, p is 0 or 1, wherein H— and Q form a chemical bond when p=0, r' is an integer from 2 to 4, w' is an integer from 1 to 50, x' is an integer from 2 to 6, y' is an integer from 0 to 5, wherein H— and Q form a chemical bond when y' is 0, r is an integer from 2 to 4, w is an integer from 1 to 50, x is an integer from 2 to 6, y is an integer from 0 to 5, wherein H— is bonded to the nitrogen of terminal —C(O)—NH— when y is 0, t is an integer from 2 to 4, u is an integer from 1 to 20, w is an integer from 1 to 50, and z is an integer from 1 to 50.

* * * * *